United States Patent
Plaza

(10) Patent No.: US 8,262,653 B2
(45) Date of Patent: Sep. 11, 2012

(54) IRRIGATED CATHETER HAVING A POROUS TIP ELECTRODE

(75) Inventor: Claudio P. Plaza, Covina, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 617 days.

(21) Appl. No.: 10/820,480

(22) Filed: Apr. 2, 2004

(65) Prior Publication Data

US 2005/0222564 A1    Oct. 6, 2005

(51) Int. Cl.
*A61B 18/14* (2006.01)
(52) U.S. Cl. .......................... 606/41; 607/105
(58) Field of Classification Search ............ 604/21; 607/120, 101–105; 606/41, 1, 48–50
See application file for complete search history.

(56) References Cited

U.S. PATENT DOCUMENTS

| | | |
|---|---|---|
| 4,819,662 A | 4/1989 | Heil, Jr. et al. |
| 4,844,099 A * | 7/1989 | Skalsky et al. .................. 607/120 |
| 5,391,199 A | 2/1995 | Ben-Haim |
| 5,443,489 A | 8/1995 | Ben-Haim |
| 5,462,521 A | 10/1995 | Brucker et al. |
| 5,546,951 A | 8/1996 | Ben-Haim |
| 5,558,091 A | 9/1996 | Acker et al. |
| 5,568,809 A | 10/1996 | Ben-Haim |
| 5,843,076 A | 12/1998 | Webster, Jr. et al. |
| 5,846,238 A * | 12/1998 | Jackson et al. .................. 606/41 |
| 5,964,757 A | 10/1999 | Ponzi |
| 6,120,476 A | 9/2000 | Fung et al. |
| 6,123,699 A | 9/2000 | Webster, Jr. |
| 6,241,666 B1 | 6/2001 | Pomeranz et al. |
| 6,405,078 B1 * | 6/2002 | Moaddeb et al. ................ 604/21 |
| 6,458,123 B1 | 10/2002 | Brucker et al. |
| 6,458,127 B1 * | 10/2002 | Truckai et al. .................. 606/49 |
| 6,466,818 B1 | 10/2002 | Moaddeb et al. |
| 7,066,935 B2 * | 6/2006 | Swoyer et al. .................. 606/41 |

FOREIGN PATENT DOCUMENTS

WO    WO 95/02995    2/1995

* cited by examiner

*Primary Examiner* — Michael Peffley
(74) *Attorney, Agent, or Firm* — Christie, Parker & Hale, LLP

(57) ABSTRACT

A porous tip electrode catheter is provided. The porous tip electrode comprises a porous material through which fluid can pass. The porous tip electrode is covered with a thin coating of conductive metal having openings through which fluids can pass.

30 Claims, 10 Drawing Sheets

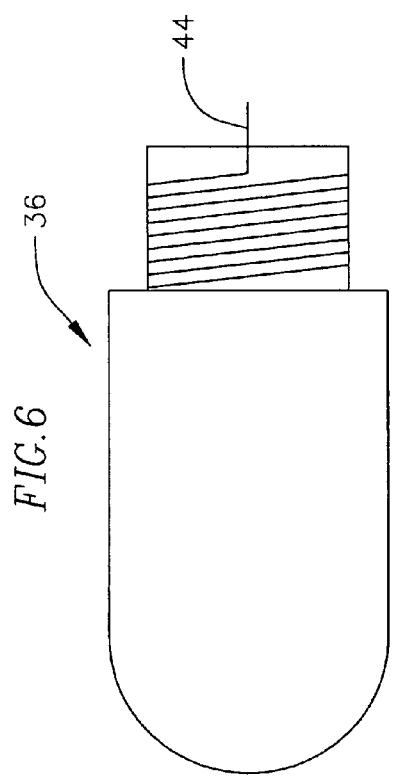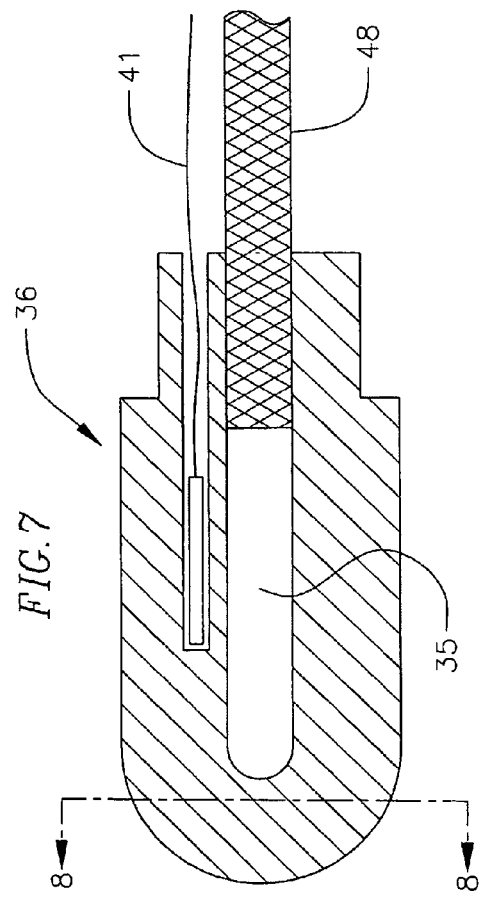

IRRIGATED CATHETER HAVING A POROUS TIP ELECTRODE

FIELD OF THE INVENTION

The present invention is directed to an irrigated catheter having a porous tip electrode.

BACKGROUND OF THE INVENTION

Electrode catheters have been in common use in medical practice for many years. They are used to map electrical activity in the heart and to ablate sites of aberrant electrical activity.

In use, the electrode catheter is inserted into a major vein or artery, e.g., the femoral artery, and then guided into the chamber of the heart which is of concern. Within the heart, the ability to control the exact position and orientation of the catheter tip is critical and largely determines the usefulness of the catheter.

In certain applications, it is desirable to have the ability to inject and/or withdraw fluid through the catheter. One such application is a cardiac ablation procedure for creating lesions which interrupt errant electrical pathways in the heart. Traditionally, this has been accomplished with an irrigated tip catheter.

A typical ablation procedure involves the insertion of a catheter having a tip electrode at its distal end into a heart chamber. A reference electrode is provided, generally taped to the patient's skin. Radio frequency (RF) current is applied to the tip electrode, and flows through the surrounding media, i.e., blood and tissue, toward the reference electrode. The distribution of current depends on the amount of electrode surface in contact with the tissue, as compared to blood which has a higher conductivity than the tissue. Heating of the tissue occurs due to its electrical resistivity. The tissue is heated sufficiently to cause cellular destruction in the cardiac tissue resulting in formation of a lesion within the cardiac tissue which is electrically non-conductive. During this process, heating of the electrode also occurs as a result of conduction from the heated tissue to the electrode itself. If the electrode temperature becomes sufficiently high, possibly above 60° C., a thin transparent coating of dehydrated blood can form on the surface of the electrode. If the temperature continues to rise, this dehydrated layer of blood can become progressively thicker resulting in blood coagulation on the electrode surface. Because dehydrated biological material has a higher electrical resistance than endocardial tissue, impedance to the flow of electrical energy into the tissue also increases. If the impedance increases sufficiently, an impedance rise occurs and the catheter must be removed from the body and the tip electrode cleaned.

In a typical application of RF current to the endocardium, circulating blood provides some cooling of the ablation electrode. However, there is typically a stagnant area between the electrode and tissue which is susceptible to the formation of dehydrated proteins and coagulum. As power and/or ablation time increases, the likelihood of an impedance rise also increases. As a result of this process, there has been a natural upper bound on the amount of energy which can be delivered to cardiac tissue and therefore the size of RF lesions. Historically, RF lesions have been hemispherical in shape with maximum lesion dimensions of approximately 6 mm in diameter and 3 to 5 mm in depth.

In clinical practice, it is desirable to reduce or eliminate impedance rises and, for certain cardiac arrythmias, to create larger lesions. One method for accomplishing this is to monitor the temperature of the ablation electrode and to control the RF current delivered to the ablation electrode based on this temperature. If the temperature rises above a pre-selected value, the current is reduced until the temperature drops below this value. This method has reduced the number of impedance rises during cardiac ablations but has not significantly increased lesion dimensions. The results are not significantly different because this method continues to rely on the cooling effect of the blood which is dependent on the location within the heart and the orientation of the catheter to the endocardial surface.

Another method is to irrigate the ablation electrode, e.g., with physiologic saline at room temperature, to actively cool the ablation electrode instead of relying on the more passive physiological cooling provided by the blood. Because the strength of the RF current is no longer limited by the interface temperature, current can be increased. This results in lesions which tend to be larger and more spherical, usually measuring about 10 to 12 mm.

The clinical effectiveness of irrigating the ablation electrode is dependent upon the distribution of flow within the electrode structure and the rate of irrigation flow through the tip. Effectiveness is achieved by reducing the overall electrode temperature and eliminating hot spots in the ablation electrode which can initiate coagulum formation. More channels and higher flows are more effective in reducing overall temperature and temperature variations, i.e., hot spots. The coolant flow rate must be balanced against the amount of fluid that can be injected into the patient and the increased clinical load required to monitor and possibly refill the injection devices during a procedure. In addition to irrigation flow during ablation, a maintenance flow, typically a lower flow rate, is required throughout the procedure to prevent backflow of blood into the coolant passages. Thus, reducing coolant flow by utilizing it as efficiently as possible is a desirable design objective.

One method for designing an ablation electrode which efficiently utilizes coolant flow is the use of a porous material structure. One such design is described in U.S. Pat. No. 6,405,078 to Moaddeb et al., the entire disclosure of which is incorporated herein by reference. Moaddeb describes the use of sintered metal particles to create a porous tip electrode. In addition, Moaddeb uses a non-conductive insert implanted into the porous tip electrode for mounting a thermocouple, lead wire and/or irrigation tube within the porous tip electrode. However, during irrigation the sintered metal particles can disintegrate and break away from the electrode structure. Consequently, a desire arises for a porous electrode having increased structural integrity.

SUMMARY OF THE INVENTION

In one embodiment, the invention is directed to an irrigated catheter having a porous tip electrode. The catheter comprises a catheter body and a tip section. The catheter body has an outer wall, proximal and distal ends, and a lumen extending therethrough. The tip section comprises a segment of flexible tubing having proximal and distal ends and at least one lumen therethrough. The proximal end of the tip section is fixedly attached to the distal end of the catheter body. The porous tip electrode is fixedly attached to the distal end of the tubing of the tip section. The tip electrode comprises a porous material through which fluid can pass.

The porous tip electrode comprises sintered non-conductive material. The sintered material may be made from any suitable non-conductive polymer or ceramic material. The sintered particles comprise both small particles and large particles, the large particles having a mean diameter at least about 2.5 times greater, and preferably, about 4 times greater, than the mean diameter of the small particles. The use of differently sized particles helps control the porosity of the sintered material, promotes uniform flow of fluid through the porous material, and minimizes fluid pressure drop through the material. The porous tip electrode is covered with a thin metal coating that is webbed, or otherwise porous, with openings through which fluid can pass to the outer surface of the tip electrode. The sintered polymeric or ceramic material has improved resistance to disintegration during irrigation. The metal coating improves overall structural stability of the tip electrode and serves as an electrode for conducting radio-frequency energy to the target tissue.

The catheter further comprises an irrigation tube having proximal and distal ends. The irrigation tube extends through the central lumen in the catheter body, with the distal end of the irrigation tube in fluid communication with the proximal end of the passage in the tip electrode. By this design, the fluid can flow through the irrigation tube, into the passage in the tip electrode and through the porous material and porous coating of the tip electrode to the outer surface of the tip electrode. A temperature sensing means is mounted in a blind hole in the tip electrode. A puller wire is mounted in the tip section. An electrode lead wire is electrically connected to the proximal end of the tip electrode.

BRIEF DESCRIPTION OF THE DRAWINGS

These and other features and advantages of the present invention will be better understood by reference to the following detailed description when considered in conjunction with the accompanying drawings wherein:

FIG. 6 is a side view of a tip electrode according to the invention depicting one method of attaching the electrode lead wire to the tip electrode;

FIG. 7 is a side cross-sectional view of a tip electrode according to the invention depicting the arrangement of the irrigation tube and temperature sensing means within the tip electrode;

DETAILED DESCRIPTION OF THE INVENTION

In a particularly preferred embodiment of the invention, there is provided a steerable catheter having an irrigated tip.

As shown in FIGS. 1 to 4, catheter 10 comprises an elongated catheter body 12 having proximal and distal ends, a tip section 14 at the distal end of the catheter body 12, and a control handle 16 at the proximal end of the catheter body 12.

Figure 1:
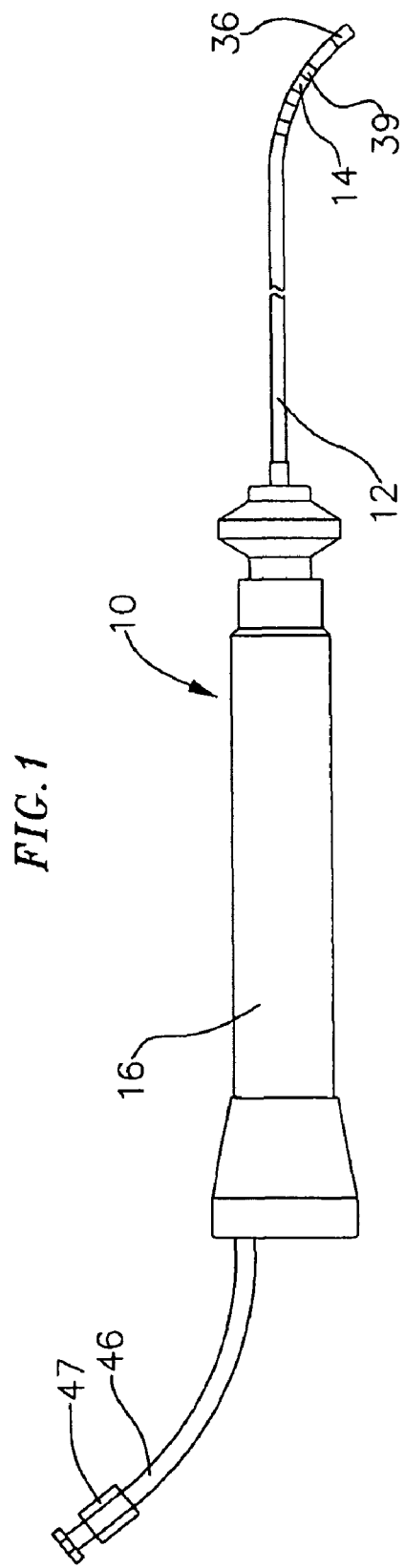
FIG. 1 is a side view of an embodiment of the catheter of the invention.
Figure 2:
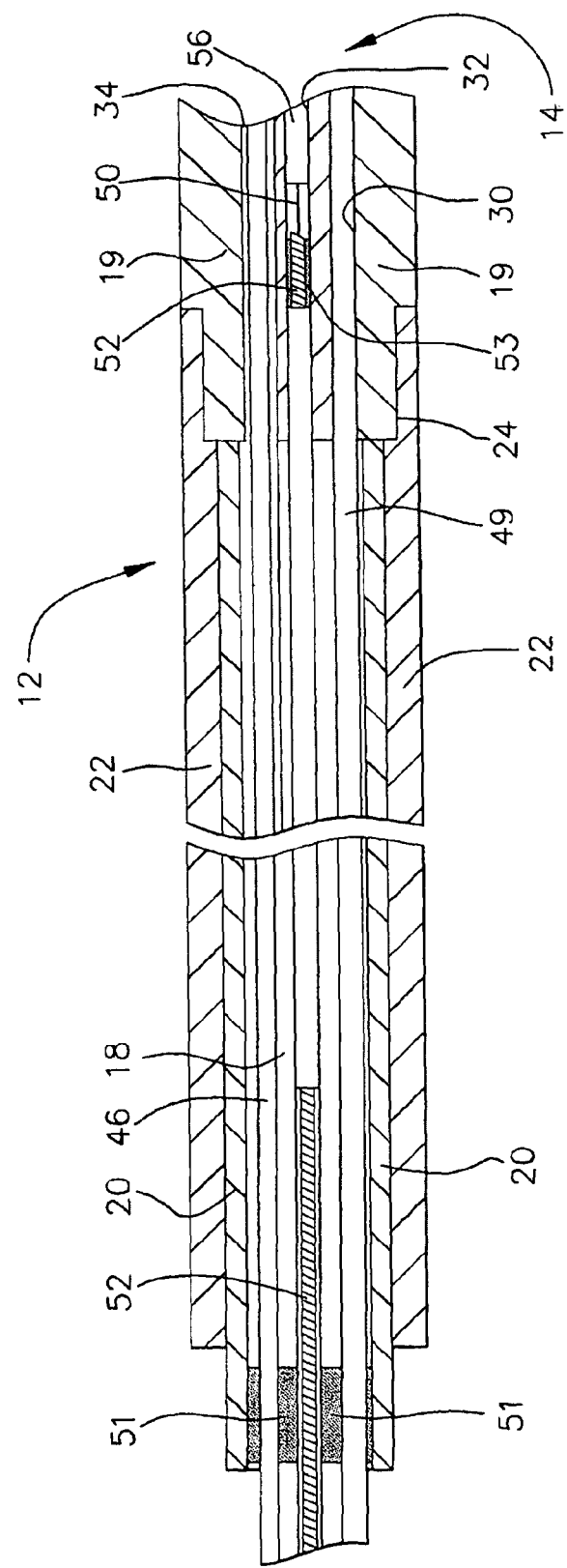
FIG. 2 is a side cross-sectional view of a catheter body according to the invention, including the junction between the catheter body and tip section.

With reference to FIG. 2, the catheter body 12 comprises an elongated tubular construction having a single, axial or central lumen 18. The catheter body 12 is flexible, i.e., bendable but substantially non-compressible along its length. The catheter body 12 can be of any suitable construction and made of any suitable material. A presently preferred construction comprises an outer wall 22 made of a polyurethane or PEBAX. The outer wall 22 comprises an imbedded braided mesh of high-strength steel, stainless steel or the like to increase torsional stiffness of the catheter body 12 so that, when the control handle 16 is rotated, the tip section 14 of the catheter 10 will rotate in a corresponding manner. The outer diameter of the catheter body 12 is not critical, but is preferably no more than about 8 french, more preferably about 7 french, still more preferably about 5 french. Likewise, the thickness of the outer wall 22 is not critical, but is thin enough so that the central lumen 18 can accommodate an irrigation tube, a puller wire, lead wires, and any other wires, cables or tubes. The inner surface of the outer wall 22 is lined with a stiffening tube 20, which can be made of any suitable material, such as polyimide or nylon. The stiffening tube 20, along with the braided outer wall 22, provides improved torsional stability while at the same time minimizing the wall thickness of the catheter, thus maximizing the diameter of the central lumen 18. The outer diameter of the stiffening tube 20 is about the same as or slightly smaller than the inner diameter of the outer wall 22. Polyimide tubing is presently preferred for the stiffening tube 20 because it may be very thin walled while still providing very good stiffness. This maximizes the diameter of the central lumen 18 without sacrificing strength and stiffness. A particularly preferred catheter has an outer wall 22 with an outer diameter of from about 0.090 inches to about 0.098 inches and an inner diameter of from about 0.061 inches to about 0.065 inches and a polyimide stiffening tube 20 having an outer diameter of from about 0.060 inches to about 0.064 inches and an inner diameter of from about 0.051 inches to about 0.056 inches.

Figure 3A:
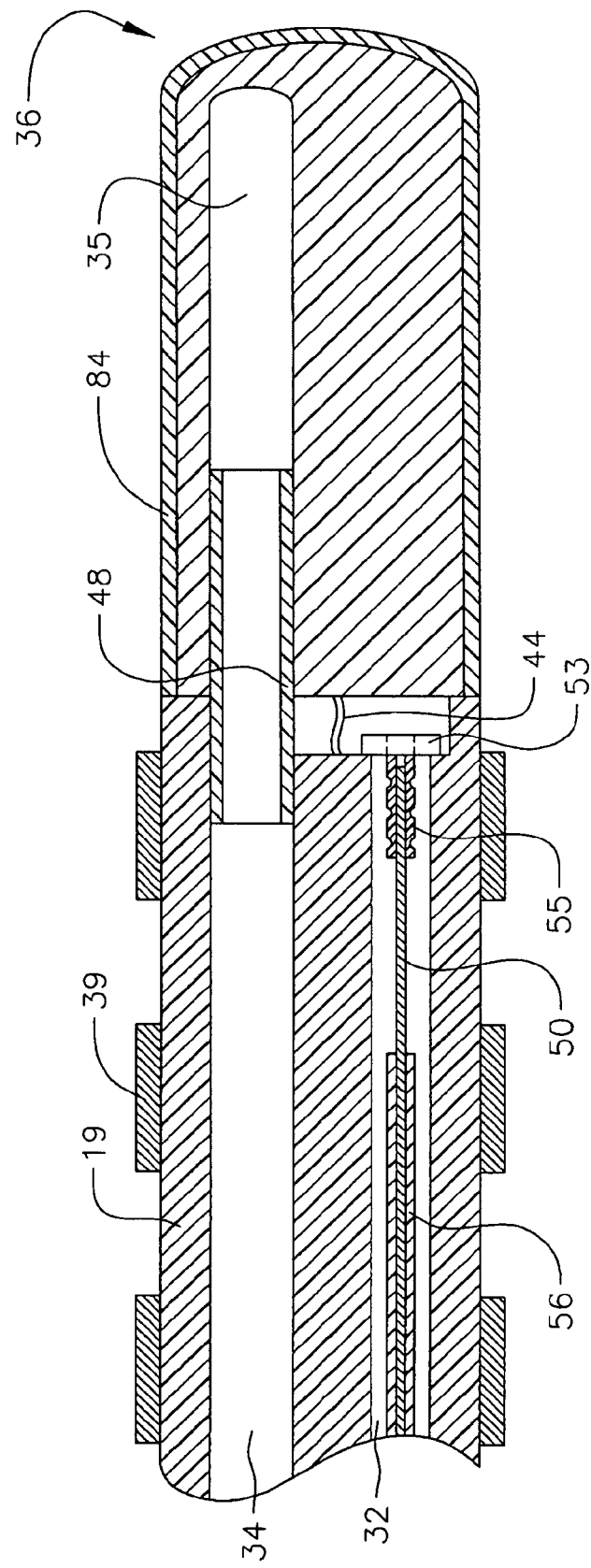
FIG. 3A is a side cross-sectional view of a catheter tip section showing the lumens for the fluid passage and puller wire.
Figure 3B:
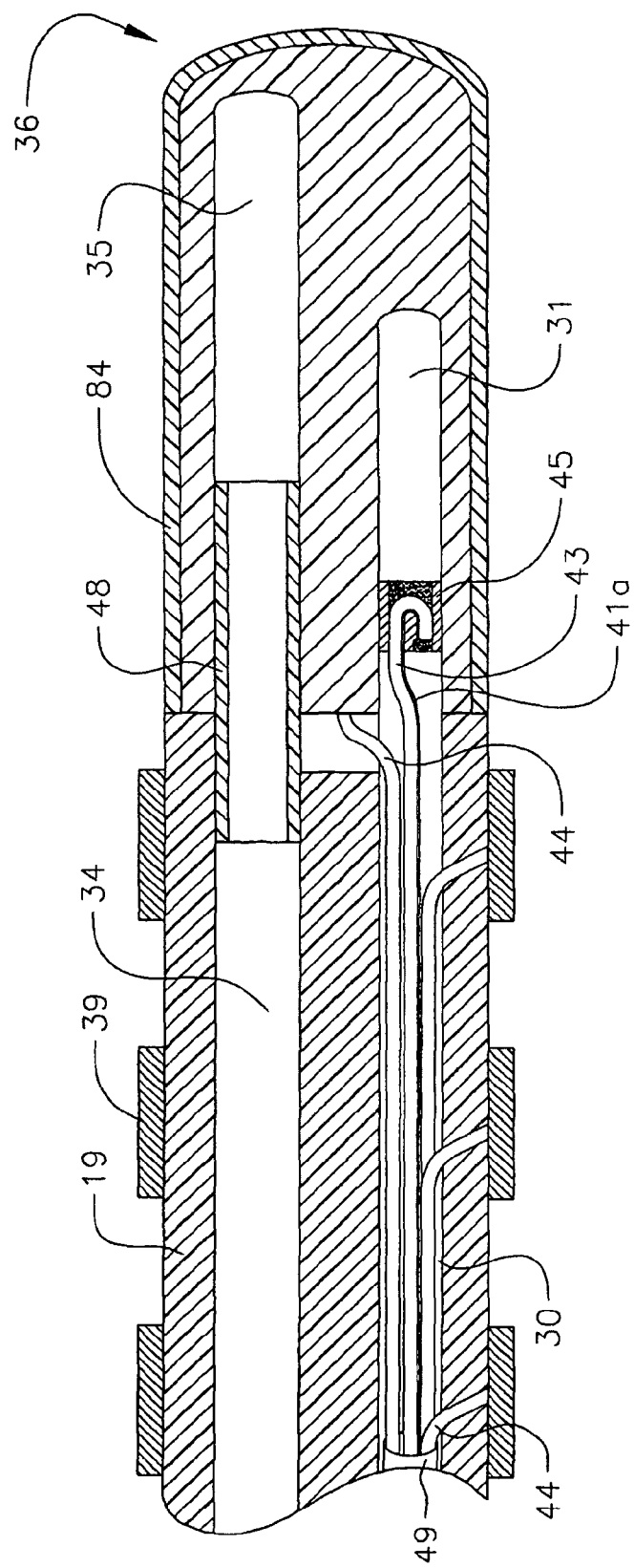
FIG. 3B is a side cross-sectional view of the catheter tip section of FIG. 3A showing the lumens for the fluid passage, thermocouple and electrode lead wires.
Figure 4:
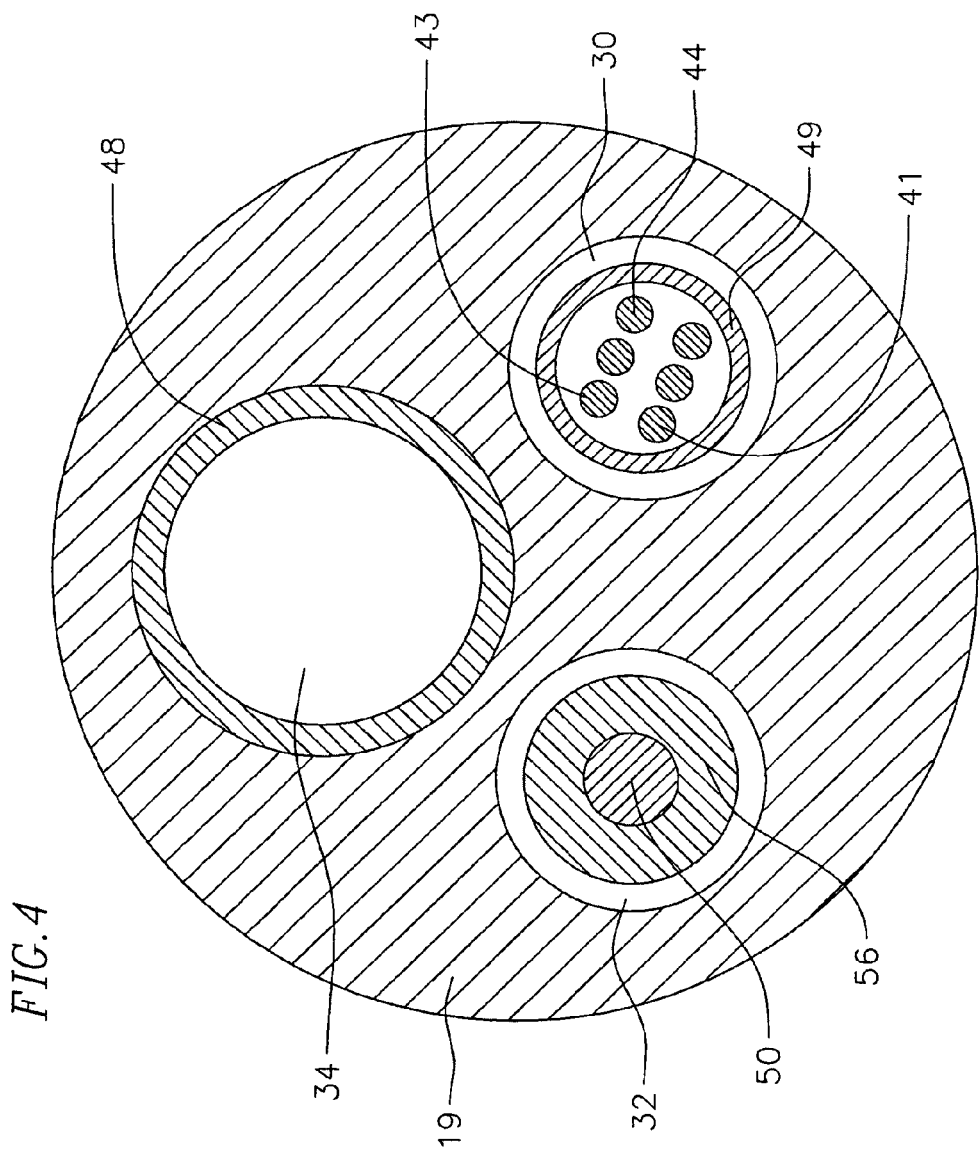
FIG. 4 is a longitudinal cross-sectional view of the tip section illustrated in FIGS. 3A and 3B.

As shown in FIGS. 3A, 3B, and 4, the tip section 14 comprises a short section of tubing 19 having three lumens 30, 32 and 34. The tubing 19 is made of a suitable non-toxic material that is preferably more flexible than the catheter body 12. A presently preferred material for the tubing 19 is braided polyurethane, i.e., polyurethane with an imbedded mesh of braided high-strength steel, stainless steel or the like. The outer diameter of the tip section 14, like that of the catheter body 12, is preferably no greater than about 8 french, more preferably about 7 french, still more preferably about 5 french. The size of the lumens is not critical. In a particularly preferred embodiment, the tip section 14 has an outer diameter of about 7 french (0.092 inches) and the first lumen 30 and second lumen 32 are generally about the same size, each having a diameter of from about 0.020 inches to about 0.024 inches, preferably about 0.022 inches, with the third lumen 34 having a slightly larger diameter of from about 0.032 inches to about 0.038 inches, preferably about 0.036 inches.

A preferred means for attaching the catheter body 12 to the tip section 14 is illustrated in FIG. 2. The proximal end of the tip section 14 comprises an outer circumferential notch 24 that receives the inner surface of the outer wall 22 of the catheter body 12. The tip section 14 and catheter body 12 are attached by adhesive (e.g. polyurethane glue) or the like. Before the tip section 14 and catheter body 12 are attached, however, the stiffening tube 20 is inserted into the catheter body 12. The distal end of the stiffening tube 20 is fixedly attached near the distal end of the catheter body 12 by forming a glue joint (not shown) with polyurethane glue or the like. Preferably, a small distance, e.g., about 3 mm, is provided between the distal end of the catheter body 12 and the distal end of the stiffening tube 20 to permit room for the catheter body 12 to receive the notch 24 of the tip section 14. A force is applied to the proximal end of the stiffening tube 20, and, while the stiffening tube 20 is under compression, a first glue joint (not shown) is made between the stiffening tube 20 and the outer wall 22 by a fast drying glue, e.g. Super Glue®. Thereafter, a second glue joint (not shown) is formed between the proximal ends of the stiffening tube 20 and outer wall 22 using a slower drying but stronger glue, e.g. polyurethane.

Figure 8:
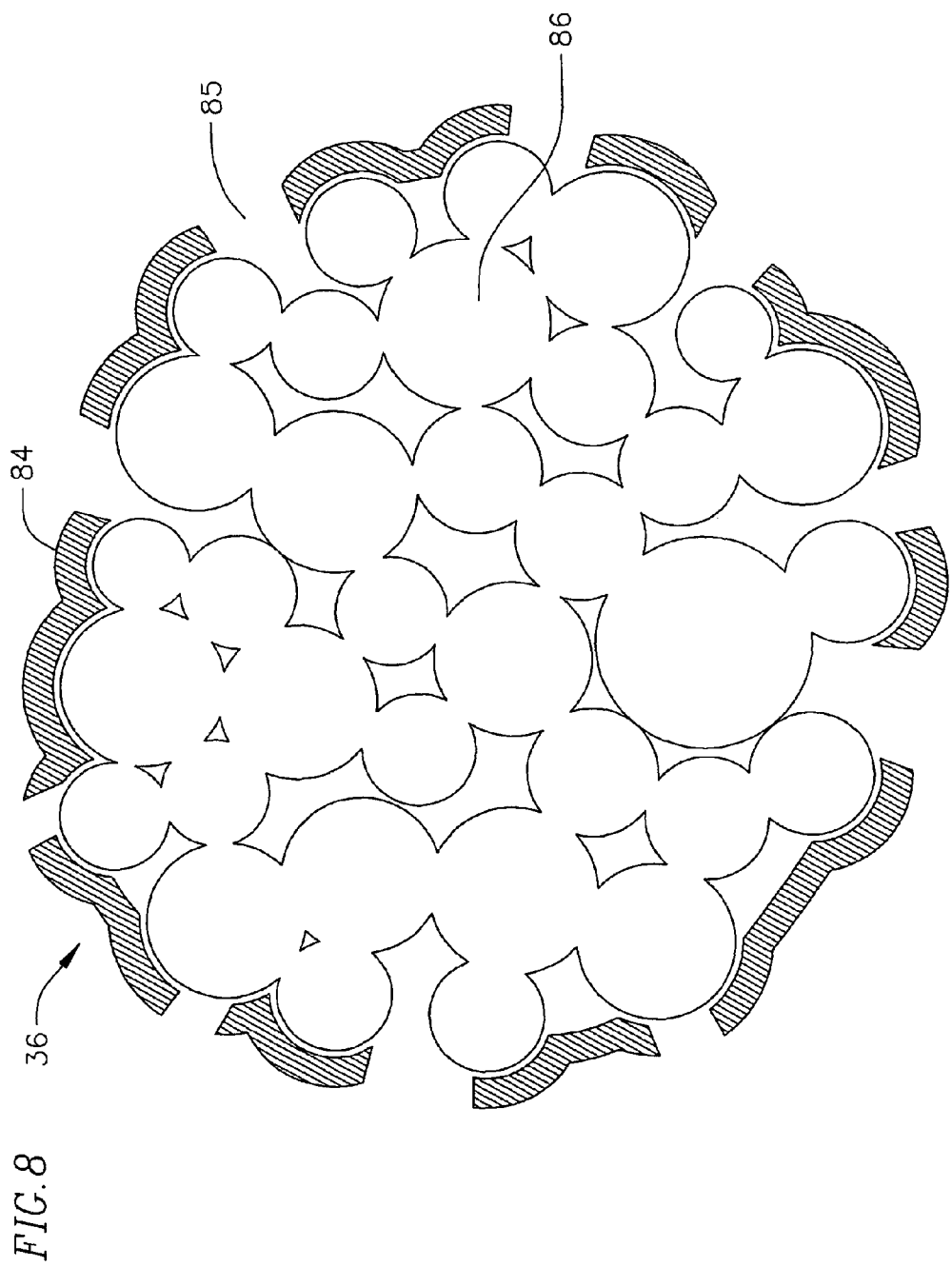
FIG. 8 is a close-up cross-sectional view of the distal section of the tip electrode taken along line 8-8 in FIG. 7.

At the distal end of the tip section 14 is a tip electrode 36. Preferably, the tip electrode 36 has a diameter about the same as the outer diameter of the tubing 19. The tip electrode 36 is formed of any suitable non-conductive polymer, such as polyethylene or Teflon®, or ceramic material, in which holes are drilled. The porous non-conductive material can be made using any conventional technique. For example, the porous non-conductive material can be machined from a rod of the material. Preferably, however, the non-conductive polymer comprises sintered polymer particles 86 formed from polyethylene or Teflon®, as best depicted in FIG. 8. As used herein, the term "sinter" refers to the process of bonding adjacent particles in a powder mass or compacting the particles by heating them to a temperature below the melting point of the main constituent at a predetermined and closely controlled time-temperature regime, including heating and cooling phases, in a protective atmosphere. The sintered polymer particles 86 permit passage of a cooling fluid through the tip electrode, as described in more detail below. The porosity of the sintered material is controlled by the amount of particle compacting in the mold or glue, the particle size, and the particle distribution.

A particularly preferred sintering process involves providing polyethylene or Teflon® powder particles in a certain sieve fraction, e.g., in the range of from about 5 microns to about 250 microns. The particles are preferably in the range of from about 10 microns to about 100 microns. In a particularly preferred embodiment, at least two different sized particles can be provided. For example, particles in the range of from about 15 microns to about 30 microns, and more preferably about 20 microns, in combination with particles in the range of from about 80 microns to about 110 microns, and more preferably about 100 microns, could be used. When two different sized particles are used, preferably the larger particles have a mean diameter at least about 2.5 times greater than the mean diameter of the smaller particles, and more preferably at least about 4 times greater. Alternatively, a single particle size can be used, which can give a denser packing and result in a higher pressure drop across the porous electrode. Whatever polymer is used, the particles are preferably rounded, and more preferably spherical, so as to provide a tip electrode surface that is not rough. However, the particles can be irregularly shaped, i.e. having differing shapes, which is a low cost alternative.

In a preferred process, the particles are put into a mold, such as a ceramic mold, having the desired electrode shape. If desired, the particles can be mixed with a suitable binder prior to being put into the mold. When a binder is used, the mold containing the binder and particles is placed into a low temperature oven and heated to a temperature sufficient to evaporate the binder. The particles are then sintered under vacuum or air at a temperature ranging from about 80° C. to about 160° C., although the temperature can vary depending on the composition of the porous polymer. However, the temperature should be below the melting point of the composition. The resulting tip electrode is then removed from the mold and assembled onto the flexible tubing of the tip section.

A tip electrode prepared in accordance with this method is depicted in FIG. 8. In particular, FIG. 8 illustrates the porosity of the tip electrode when particles of different sizes are used. Although the drawings of the tip electrode, such as FIGS. 3A and 3B, do not depict the porous sintered material in detail, it is to be understood that where the body of the tip electrode is described as being made of a porous sintered material, it appears generally as depicted in FIG. 8. The drawings, such as FIGS. 3A and 3B, are provided to more clearly show the additional components in the tip section.

As shown in FIGS. 3A and 3B, the tip electrode 36 has two cavities extending therein, namely a primary fluid passage 35 and a blind hole 31 that correspond in size and location to the lumens 34 and 30, respectively, in the tip section 14. The primary fluid passage 35 extends substantially all the way through the sintered material of the tip electrode 36, preferably ending just before the distal end of the tip electrode 36. The blind hole 31 extends only a part of the way through the sintered material of the tip electrode 36, preferably about half the length of the tip electrode 36 or less. For example, for a 3.5 mm tip electrode 36, the blind hole 31 is about 0.088 inches long.

Figure 10:
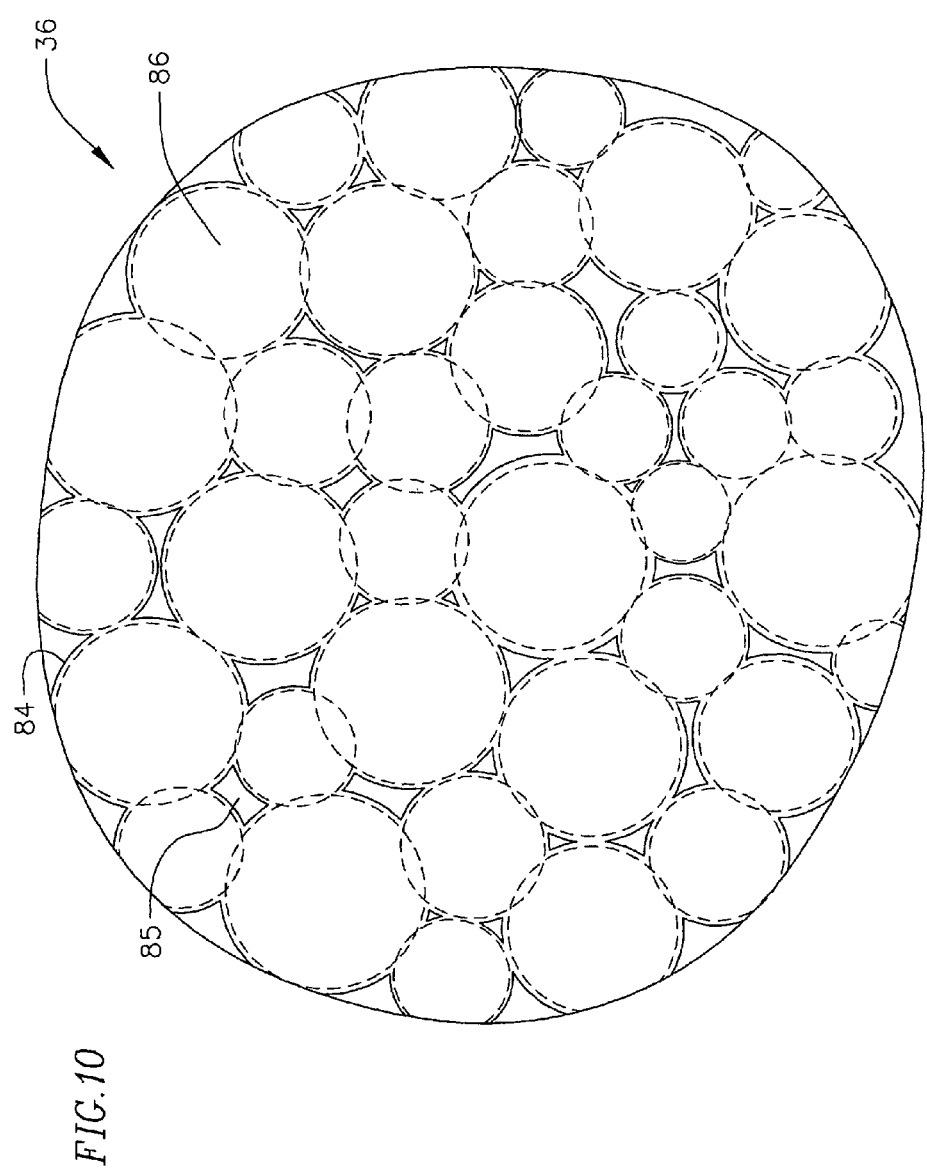
FIG. 10 is a close-up view of a portion of the surface of the tip electrode depicting one embodiment of the porous coating disposed over the porous surface of the tip electrode.

Disposed over the surface of the porous tip electrode is a thin metal coating 84, as depicted in FIG. 10. The metal coating 84 serves to impart improved structural integrity to the porous tip electrode 36 while also serving as an electrode for distributing radio-frequency energy to the target tissue. The metal coating also prevents substantial contact of the non-conductive porous material of the tip electrode with the target tissue. The metal coating 84 can be made of any conductive metal, e.g. platinum or gold. Preferably, the metal coating 84 is made of a platinum-iridium alloy, e.g. 90% Platinum/10% Iridium, applied to the surface of the porous tip electrode 36 by a deposition process impregnating a thin layer of platinum-iridium alloy onto the porous surface of the tip electrode 36. The thickness of the metal coating 84 may vary as desired, but is sufficiently thin to maintain a porous electrode surface, and sufficiently thick to maintain a conductive surface. For example, the metal coating 84 may have a thickness ranging from 0.2 μm to about 2 μm. Preferably, as shown in FIG. 10, the metal coating 84 is webbed or otherwise porous with openings 85 in the metal coating 84 through which irrigation fluids can pass.

A preferred tip electrode has a length ranging from about 2.5 mm to about 8 mm, preferably about 3.5 mm. Preferably, the tip electrode 36 is attached to the tubing 19 by polyurethane glue or the like. The wires and tubes that extend into the tip electrode 36, described in more detail below, help to keep the tip electrode in place on the tubing 19 of the tip section 14.

In the embodiment shown in FIGS. 3A and 3B, there are three ring electrodes 39 mounted on the tubing 19 proximal to the tip electrode 36. It is understood that the presence and number of ring electrodes 39 may vary as desired. Each ring electrode 39 is slid over the tubing 19 and fixed in place by glue or the like. The ring electrodes 39 can be made of any suitable material, and are preferably machined from platinum-iridium bar (90% platinum/10% iridium).

The tip electrode 36 and ring electrodes 39 are each connected to a separate lead wire 44. The lead wires 44 extend through the first lumen 30 of tip section 14, the central lumen 18 of the catheter body 12, and the control handle 16, and terminate at their proximal ends in an input jack (not shown) that may be plugged into an appropriate monitor (not shown).

The portion of the lead wires 44 extending through the central lumen 18 of the catheter body 12, control handle 16 and proximal end of the tip section 14 may be enclosed within a protective sheath 49, which can be made of any suitable material, preferably polyimide. The protective sheath 49 is preferably anchored at its distal end to the proximal end of the tip section 14 by gluing it in the first lumen 30 with polyurethane glue or the like. The lead wires 44 are attached to the tip electrode 36 and ring electrodes 39 by any conventional technique. For example, as described below, the tip electrode 36, in one embodiment, may have a distal section 70 having a greater diameter than the diameter of proximal section 68. In this embodiment, as depicted in FIG. 6, connection of a lead wire 44 to the tip electrode is accomplished, for example, by coiling the lead wire 44 around the proximal portion of the tip electrode 36 and gluing it in place to the metal coating 84 with polyurethane glue or the like.

Connection of a lead wire 44 to a ring electrode 39 is preferably accomplished by first making a small hole through the tubing 19. Such a hole can be created, for example, by inserting a needle through the tubing 19 and heating the needle sufficiently to form a permanent hole. A lead wire 44 is then drawn through the hole by using a microhook or the like. The ends of the lead wire 44 are then stripped of any coating and soldered or welded to the underside of the ring electrode 39, which is then slid into position over the hole and fixed in place with polyurethane glue or the like.

An irrigation tube is provided within the catheter body 12 for infusing fluids, e.g. saline, to cool the tip electrode 36. The irrigation tube may be made of any suitable material, and is preferably made of polyimide tubing. A preferred irrigation tube has an outer diameter of from about 0.032 inches to about 0.036 inches and an inner diameter of from about 0.027 inches to about 0.032 inches.

With reference to FIGS. 2 and 3A, the irrigation tube comprises multiple tube segments. A first irrigation tube segment 46 extends through the central lumen 18 of the catheter body 12 and terminates in the proximal end of the third lumen 34 of the tip section 14. The distal end of the first irrigation tube segment 46 is anchored in the third lumen 34 by polyurethane glue or the like. The proximal end of the first irrigation tube segment 46 extends through the control handle 16 and terminates in a luer hub 47 or the like at a location proximal to the control handle. A second irrigation tube segment 48 is provided at the distal end of the third lumen 34 and extends into the primary fluid passage 35 of the tip electrode 36. The second irrigation tube segment 48 is anchored by polyurethane glue or the like within the third lumen 34 of the tip section 14 and in the primary fluid passage 35. The second irrigation tube segment 48 provides additional support to maintain the tip electrode 36 mounted on the tubing 19. In practice, fluid is injected into the first irrigation tube segment 46, through the third lumen 34, through the second irrigation tube segment 48, into the primary fluid passage 35 of the tip electrode 36, and out through the porous material of the tip electrode. Because the primary fluid passage 35 extends distally a greater length than the blind hole 31, the fluid can pass outwardly on all sides of the distal end of the primary fluid passage 35.

The fluid introduced through the catheter is preferably a biologically compatible fluid, and may be in a gaseous or liquid state. Suitable fluids include saline, water, carbon dioxide, nitrogen, and helium. In addition to, or instead of, being used to cool the tip electrode, the infused fluid also forms a buffer layer to maintain biological materials, such as blood, at a distance from the tip electrode, thereby minimizing contact of the tip electrode with the biological material. This buffer layer reduces coagulation of biological materials and regulates the impedance or resistance to energy transfer of the tissue near the tip electrode-during ablation.

The rate of fluid flow through the catheter may be controlled by any suitable fluid infusion pump or by pressure. A suitable infusion pump is the FLOGARD™ available from Baxter. The rate of fluid flow through the catheter preferably ranges from about 0.5 ml/min to about 30 ml/min, more preferably from about 5 ml/min to about 15 ml/min. Preferably, the fluid is maintained at about room temperature.

As shown in FIG. 7, a temperature sensing means 41 is provided for the tip electrode 36 and, if desired, the ring electrodes 39. Any conventional temperature sensing means 41, e.g., a thermocouple or thermistor, may be used. With reference to FIG. 3B, a preferred temperature sensing means 41 for the tip electrode 36 comprises a thermocouple formed by a wire pair. One wire of the wire pair is a copper wire 41a, e.g., a number 40 copper wire. The other wire of the wire pair is a constantan wire 43, which gives support and strength to the wire pair. The wires 41a and 43 of the wire pair are electrically isolated from each other except at their distal ends where they contact each other and are twisted together, covered with a short piece of plastic tubing 45, e.g. polyimide, and covered with epoxy. The plastic tubing 45 is then attached by polyurethane glue or the like in the first blind hole 31 of the tip electrode 36. The wires 41a and 43 extend through the first lumen 30 in the tip section 14. Within the catheter body 12, the wires 41a and 43 may extend through the protective sheath 49 with the lead wires 44. The wires 41a and 43 then extend out through the control handle 16 and to a connector (not shown) connectable to a temperature monitor (not shown).

Alternatively, the temperature sensing means 41 may be a thermistor. A suitable thermistor for use in the present invention is Model No. AB6N2-GC14KA143E/37C sold by Thermometrics (New Jersey). The temperature sensing means may also be used as a feedback system to adjust the flow rate of the fluid through the catheter to maintain a desired temperature at the tip electrode.

A puller wire 50 extends through the catheter body 12, is anchored at its proximal end to the control handle 16, and is anchored at its distal end to the tip section 14. The puller wire 50 is made of any suitable metal, such as stainless steel or Nitinol, and is preferably coated with Teflon® or the like. The coating imparts lubricity to the puller wire 50. The puller wire 50 preferably has a diameter ranging from about 0.006 inches to about 0.010 inches.

A compression coil 52 is situated within the catheter body 12 in surrounding relation to the puller wire 50. The compression coil 52 extends from the proximal end of the catheter body 12 to the proximal end of the tip section 14. The compression coil 52 is made of any suitable metal, preferably stainless steel. The compression coil 52 is tightly wound on itself to provide flexibility, i.e., bending, but to resist compression. The inner diameter of the compression coil 52 is preferably slightly larger than the diameter of the puller wire 50. The Teflon® coating on the puller wire 50 allows it to slide freely within the compression coil 52. If desired, particularly if the lead wires 44 are not enclosed by a protective sheath 49, the outer surface of the compression coil 52 can be covered by a flexible, non-conductive sheath, e.g., made of polyimide tubing, to prevent contact between the compression coil 52 and any other wires within the catheter body 12.

The compression coil 52 is anchored at its proximal end to the proximal end of the stiffening tube 20 in the catheter body 12 by glue joint 51 and at its distal end to the tip section 14 by glue joint 53. Both glue joints 52 and 53 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 22 of the catheter body 12 and stiffening tube 20 which is heated sufficiently to form a permanent hole. The glue is then introduced through the hole to the outer surface of the compression coil 52 and wicks around the outer circumference to form a glue joint about the entire circumference of the compression coil 52.

Figure 9:
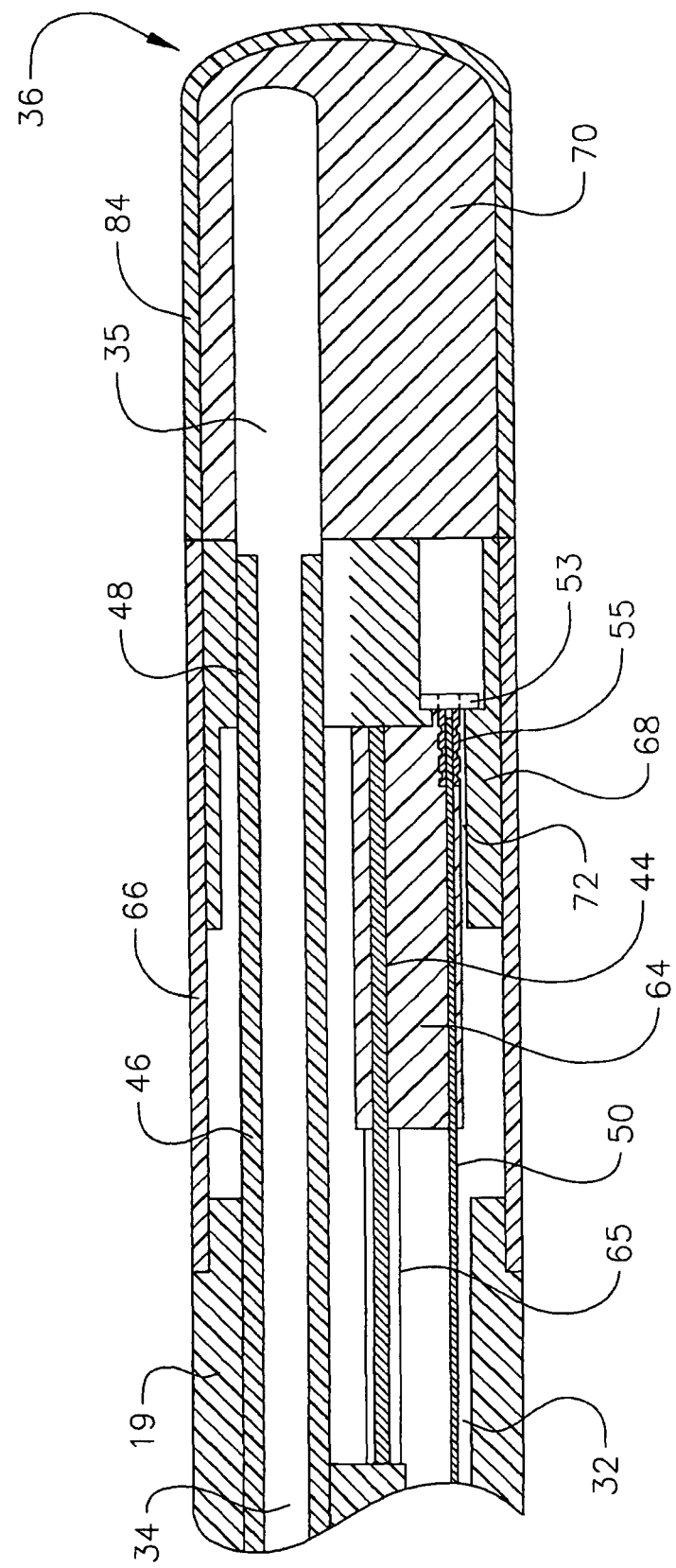
FIG. 9 is a side cross-sectional view of an alternative tip section according to the invention that houses an electromagnetic sensor.

The puller wire 50 extends into the second lumen 32 of the tip section 14. The puller wire 50 is anchored at its distal end to the tip section 14. Preferably, an anchor is fixedly attached to the distal end of the puller wire 50, as depicted in FIGS. 3A and 9. The anchor is preferably formed by a metal tube 55, e.g. a short segment of hypodermic stock, which is fixedly attached, e.g. by crimping, to the distal end of the puller wire 50. The tube 55 has a section that extends a short distance beyond the distal end of the puller wire 50. A cross-piece 53 made of a small section of stainless steel ribbon or the like is soldered or welded in a transverse arrangement to the distal end of the tube section 55, which is flattened during the operation. This creates a T-bar anchor. A notch is created in the side of the tip section 14, resulting in an opening into the second lumen 32 into which the puller wire 50 extends. The anchor lies partially within the notch. Because the length of the ribbon forming the cross-piece 53 is longer than the diameter of the opening into the lumen 32, the anchor cannot be pulled completely into the lumen 32. The notch is then sealed with polyurethane glue or the like to give a smooth outer surface. Within the second lumen 32 of the tip section 14, the puller wire 50 extends through a plastic, preferably Teflon® sheath 56, which prevents the puller wire 50 from cutting into the wall of the tubing 19 when the tip section is deflected.

Figure 5:
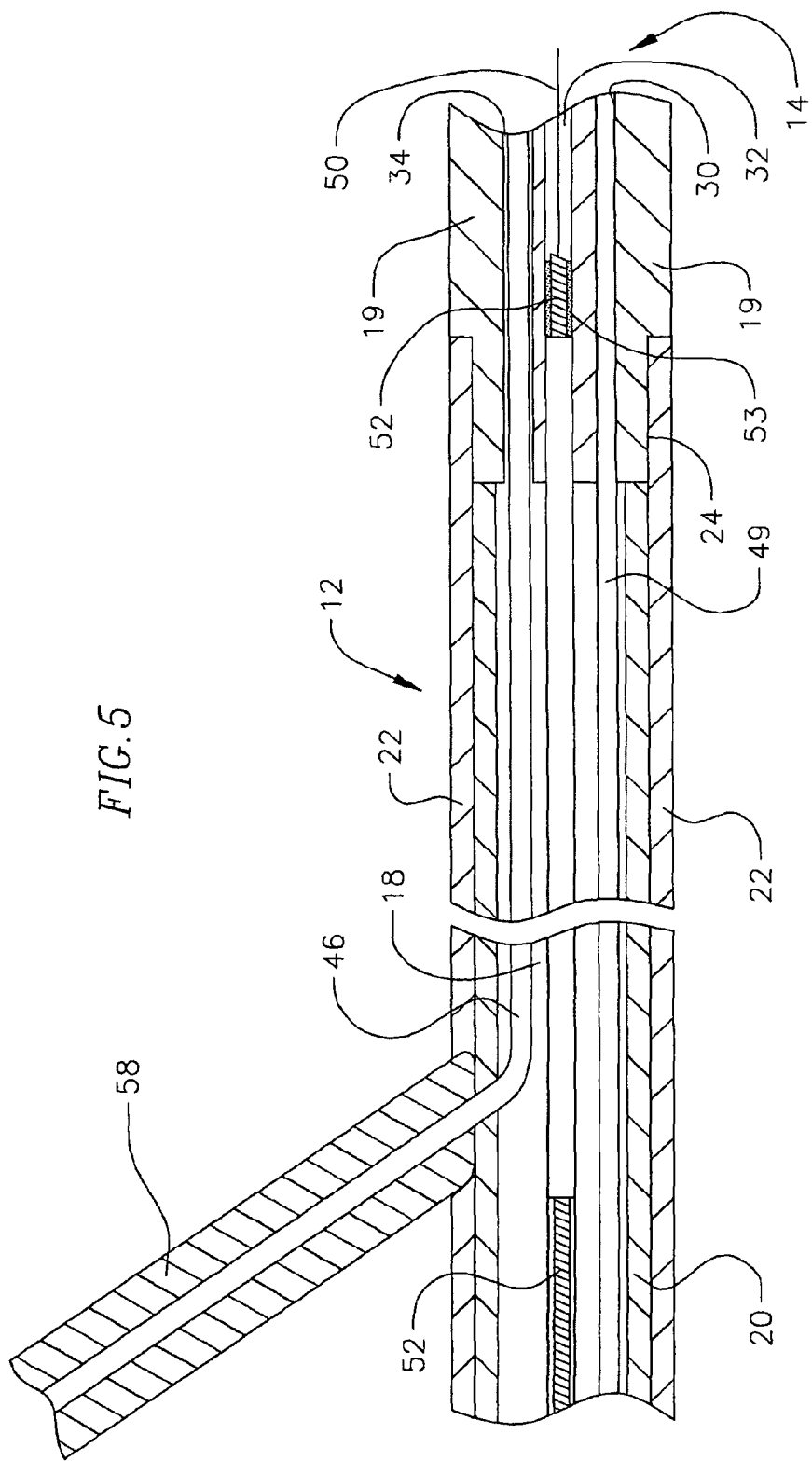
FIG. 5 is a side cross-sectional view of an alternative embodiment of a catheter body according to the invention having a side arm for an irrigation tube.

In an alternative arrangement, as shown in FIG. 5, a single lumen side arm 58 is fluidly connected to the central lumen 18 near the proximal end of the catheter body 12. The first irrigation tube segment 46 extends through the catheter body 12 and out the side arm 58, where it terminates in a luer hub (not shown) or the like. The side arm 58 is preferably made of the same material as the outer wall 22, but preferably has a greater thickness, e.g. 0.0275 inches. Where the side arm 58 meets the catheter body 12, a molded joint can be provided to provide additional strength and support. The molded joint can be made of any suitable biocompatible material, and is preferably made of polyurethane.

Longitudinal movement of the puller wire 50 relative to the catheter body 12, which results in deflection of the tip section 14, is accomplished by suitable manipulation of the control handle 16. A suitable control handle for use with the present invention is described in U.S. Pat. No. 6,120,476, the disclosure of which is incorporated herein by reference.

In another preferred embodiment according to the invention, an electromagnetic sensor 64 is provided in the distal end of the tip section 14. As shown in FIG. 9, in this embodiment the tip electrode 36 is connected to the tubing 19 of the tip section 14 by means of a plastic housing 66, preferably made of polyetheretherketone (PEEK). The tip electrode 36 has a proximal section 68 and a distal section 70. The proximal section 68 of the tip electrode 36 has an outer diameter less than the outer diameter of the distal section 70. Thus, in the depicted embodiment, the proximal section 68 forms a recessed stem that fits inside the distal end of the plastic housing 66, and the distal section 70 is exposed. The proximal section 68 is bonded to the housing 66 by polyurethane glue or the like. The proximal end of the plastic housing 66 is bonded with polyurethane glue or the like to the distal end of the tubing 19 of the tip section 14. Preferably, the plastic housing 66 is about 1 cm long.

In this embodiment, the tip electrode 36 preferably has a total length ranging from about 6 mm to about 9 mm, more preferably about 7 mm. For a 7 mm long tip electrode, the distal section 70 and proximal section 68 each preferably have a length of about 3.5 mm. The proximal section 68 is formed of a solid metal material. The distal section 70 is formed of a porous material, as described above. However, the tip electrode 36 could be modified so that a portion of the proximal section 68, which is formed of a solid material, is exposed along with the distal section 70, which is formed of a porous material. Alternatively, a portion of the distal section 70 could form a part of the stem that extends into the housing 66. However, in the preferred embodiment, the entire porous distal section 70 is exposed and the entire solid proximal section 68 is contained within the housing 66.

A generally hollow cavity 72 is formed in the proximal end of the proximal section 68 of the tip electrode 36. The electromagnetic sensor 64 is mounted partially in the plastic housing 66, partially in the cavity 72, and partially in the flexible tubing 19, in a manner similar to that described in U.S. Pat. No. 6,120,476, the disclosure of which is incorporated herein by reference.

The tip electrode 36 has a fluid passage 35 and a blind hole 31 that extend longitudinally from the cavity 72. The second irrigation tube segment 48, puller wire 50, thermocouple wires 41 and 43, and tip electrode lead wire 44 are mounted in the tip electrode. The electromagnetic sensor 64 is connected to an electromagnetic sensor cable 65, which extends through the third lumen 34 of the tip section 14, through the central lumen 18 of the catheter body 12, and into the control handle 16. The electromagnetic sensor cable 65 then extends out the proximal end of the control handle 16 within an umbilical cord (not shown) to a sensor control module (not shown) that houses a circuit board (not shown). Alternatively, the circuit board can be housed within the control handle 16, for example, as described in U.S. Pat. No. 5,964,757, the disclosure of which is incorporated herein by reference. The electromagnetic sensor cable 65 comprises multiple wires encased within a plastic covered sheath. In the sensor control module, the wires of the electromagnetic sensor cable are connected to the circuit board. The circuit board amplifies the signal received from the electromagnetic sensor and transmits it to a computer in a form understandable by the computer by means of the sensor connector at the proximal end of the sensor control module. Also, because the catheter is designed for single use only, the circuit board preferably contains an EPROM chip which shuts down the circuit board approximately 24 hours after the catheter has been used. This prevents the catheter, or at least the electromagnetic sensor, from being used twice. Suitable electromagnetic sensors for use with the present invention are described, for example, in U.S. Pat. Nos. 5,558,091, 5,443,489, 5,546,951, 5,568,809 and 5,391,199 and International Publication No. WO 95/02995, the disclosures of which are incorporated herein by reference. A preferred electromagnetic sensor 64 has a length of from about 6 mm to about 7 mm and a diameter of about 1.3 mm.

Preferably, in this embodiment, the catheter body does not comprise a stiffening tube 20, because additional space is needed within the central lumen 10 to include the electromagnetic sensor cable. The catheter body in this embodiment has an outer diameter preferably no greater than about 8 french, more preferably from about 7 french to about 7.5 french, and if desired, no greater than about 5 french.

In the above-described embodiments, the tip electrode is described as having a fluid passage and a blind hole. As would be recognized by one skilled in the art, the tip electrode could have only a fluid passage into which all of the tubes, wires, etc. extend. However, such a design is less desirable because the thermocouple would be in direct contact with the fluid, which can result in an inaccurate temperature reading.

If desired, the catheter can be multidirectional, i.e., having two or more puller wires to enhance the ability to manipulate the tip section in more than one direction or to form two or more different curves. Such a design is described in U.S. Pat. No. 6,123,699, the disclosure of which is incorporated herein by reference.

The preceding description has been presented with reference to presently preferred embodiments of the invention. Workers skilled in the art and technology to which this invention pertains will appreciate that alterations and changes in the described structure may be practiced without meaningfully departing from the principle, spirit and scope of this invention. Accordingly, the foregoing description should not be read as pertaining only to the precise structures described and illustrated in the accompanying drawings, but rather should be read consistent with and as support for the following claims, which are to have their fullest and fairest scope.

What is claimed is:

1. An irrigated electrode catheter for ablating tissue, the catheter comprising:
    a catheter body having proximal and distal ends and a lumen extending therethrough;
    a tip section having proximal and distal ends, the proximal end of the tip section being fixedly attached to the distal end of the catheter body;
    a porous tip electrode fixedly attached to the distal end of the tip section, the tip electrode comprising a non-conductive porous material and a conductive porous coating adapted to cover the non-conductive porous material, wherein the conductive porous coating has a thickness of about 0.2 µm to about 2 µm; and
    an irrigation tube extending through the catheter body and into the porous tip electrode of the tip section, whereby fluid passing through the irrigation tube can pass through the non-conductive porous material and the conductive porous coating to reach surrounding tissue.

2. An irrigated electrode catheter according to claim 1, further comprising an electrode lead wire in electrical communication with the conductive porous coating.

3. An irrigated electrode catheter according to claim 1, wherein the non-conductive porous material is made from a material selected from the group consisting of polyethylene, Teflon and ceramic.

4. An irrigated electrode catheter according to claim 1, wherein the non-conductive porous material comprises polyethylene.

5. An irrigated electrode catheter according to claim 1, wherein the conductive porous coating is made from a material selected from the group consisting of platinum and gold.

6. An irrigated electrode catheter according to claim 1, wherein the conductive porous coating comprises an alloy of platinum and iridium.

7. An irrigated electrode catheter according to claim 6, wherein the alloy of platinum and iridium comprises 90% platinum and 10% iridium.

8. An irrigated electrode catheter according to claim 1, wherein fluid passes through channels between particles of the non-conductive porous material.

9. An irrigated electrode catheter according to claim 1, wherein fluid passes through channels of a webbing of the conductive porous coating.

10. An irrigated electrode catheter according to claim 1, further comprising a temperature sensing means mounted within the tip electrode.

11. An irrigated electrode catheter according to claim 1, further comprising an electromagnetic sensor mounted in the tip section.

12. An irrigated electrode catheter according to claim 1, wherein the non-conductive porous material comprises sintered polymer particles.

13. An irrigated electrode catheter according to claim 1, wherein the non-conductive porous material comprises sintered ceramic particles.

14. An irrigated electrode catheter according to claim 12, wherein the polymer particles comprises particles of polyethylene or Teflon.

15. An irrigated electrode catheter for ablating tissue, the catheter comprising:
    a catheter body having an outer wall, proximal and distal ends, and a lumen extending therethrough;
    a tip section comprising a segment of flexible tubing having proximal and distal ends and at least one lumen therethrough, the proximal end of the tip section being fixedly attached to the distal end of the catheter body;
    a porous tip electrode fixedly attached to the distal end of the tubing of the tip section, the tip electrode having an outer surface and comprising a non-conductive porous material through which fluid can pass and a thin metal coating adapted to cover the non-conductive porous material, wherein the thin metal coating has a thickness of about 0.2 µm to about 2 µm; and
    an irrigation tube having proximal and distal ends extending through the central lumen in the catheter body, wherein the distal end of the irrigation tube is in fluid communication with a proximal end of a passage in the tip electrode, whereby fluid can pass through the irrigation tube, into the passage in the tip electrode and through the porous material of the tip electrode to the outer surface of the tip electrode.

16. An irrigated electrode catheter according to claim 15, further comprising an electrode lead wire in electrical communication with the thin metal coating.

17. An irrigated electrode catheter according to claim 15, wherein the non-conductive porous material is made from a material selected from the group consisting of polyethylene, Teflon and ceramic.

18. An irrigated electrode catheter according to claim 15, wherein the non-conductive porous material comprises polyethylene.

19. An irrigated electrode catheter according to claim 15, wherein the thin metal coating is made from a material selected from the group consisting of platinum and gold.

20. An irrigated electrode catheter according to claim 15, wherein the thin metal coating comprises an alloy of platinum and iridium.

21. An irrigated electrode catheter according to claim 20, wherein the alloy of platinum and iridium comprises 90% platinum and 10% iridium.

22. An irrigated electrode catheter according to claim 15, wherein fluid passes through channels between particles of the non-conductive porous material.

23. An irrigated electrode catheter according to claim 15, wherein fluid passes through channels of a webbing of the thin metal coating.

24. An irrigated electrode catheter according to claim 15, further comprising a temperature sensing means mounted within the tip electrode.

25. An irrigated electrode catheter according to claim 15, further comprising an electromagnetic sensor mounted in the tip section.

26. An irrigated electrode catheter according to claim 15, wherein the non-conductive porous material comprises sintered polymer particles.

27. An irrigated electrode catheter according to claim 15, wherein the non-conductive porous material comprises sintered ceramic particles.

28. An irrigated electrode catheter according to claim 26, wherein the polymer particles comprise particles of polyethylene or Teflon.

29. An irrigated electrode catheter for ablating tissue, the catheter comprising:
   a catheter body;
   a tip section attached to the catheter body;
   a porous tip electrode fixedly attached to the tip section, the tip electrode comprising a non-conductive porous material and a conductive porous coating generally encapsulating the non-conductive porous material, wherein the conductive porous coating has a thickness of about 0.2 µm to about 2 µm; and
   an irrigation tube extending through the catheter body and into the porous tip electrode of the tip section, whereby fluid passing through the irrigation tube can pass through the non-conductive porous material and the conductive porous coating to reach surrounding tissue.

30. An irrigated electrode catheter for ablating tissue, the catheter comprising:
   a catheter body;
   a tip section attached to the catheter body;
   a porous tip electrode fixedly attached to the tip section, the tip electrode comprising an inner non-conductive porous material and an outer conductive porous material, wherein the outer conductive porous material has a thickness of about 0.2 µm to about 2 µm; and
   an irrigation tube extending through the catheter body and into the porous tip electrode of the tip section, whereby fluid passing through the irrigation tube can pass through the non-conductive porous material and the conductive porous material to reach surrounding tissue.

* * * * *

UNITED STATES PATENT AND TRADEMARK OFFICE
CERTIFICATE OF CORRECTION

| | |
|---|---|
| PATENT NO. | : 8,262,653 B2 |
| APPLICATION NO. | : 10/820480 |
| DATED | : September 11, 2012 |
| INVENTOR(S) | : Claudio P. Plaza |

Page 1 of 1

It is certified that error appears in the above-identified patent and that said Letters Patent is hereby corrected as shown below:

In the Claims

Column 12, Claim 14, line 14　　　Delete "comprises"
　　　　　　　　　　　　　　　　Insert -- comprise --

Signed and Sealed this
Twenty-ninth Day of October, 2013

Teresa Stanek Rea
*Deputy Director of the United States Patent and Trademark Office*